United States Patent
Schwab et al.

(10) Patent No.: US 6,232,482 B1
(45) Date of Patent: May 15, 2001

(54) METHOD FOR PRODUCING RUTHENIUM COMPLEXES

(75) Inventors: Peter Schwab, Bad Dürkheim; Michael Schulz, Ludwigshafen; Justin Wolf, Weikersheim; Wolfram Stuer; Helmut Werner, both of Würzburg, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/485,854

(22) PCT Filed: Aug. 20, 1998

(86) PCT No.: PCT/EP98/05303

§ 371 Date: May 8, 2000

§ 102(e) Date: May 8, 2000

(87) PCT Pub. No.: WO99/10356

PCT Pub. Date: Mar. 4, 1999

(30) Foreign Application Priority Data

Aug. 22, 1997 (DE) .............................. 197 36 609
Jan. 13, 1998 (DE) .............................. 198 00 934

(51) Int. Cl.[7] .............................. C07F 9/00; C07F 15/00; B01J 31/00
(52) U.S. Cl. .............................. 556/21; 556/136; 556/137; 502/155
(58) Field of Search .............................. 556/21, 136, 137; 502/155

(56) References Cited

U.S. PATENT DOCUMENTS

| | | | |
|---|---|---|---|
| 5,342,909 | * 8/1994 | Grubbs et al. | 526/171 |
| 5,831,108 | * 11/1998 | Grubbs et al. | 556/21 |
| 5,849,851 | * 12/1998 | Grubbs et al. | 526/93 |
| 5,990,340 | * 11/1999 | Haider at al. | 560/25 |

FOREIGN PATENT DOCUMENTS

WO 93/2011   10/1993   (WO) .
WO 96/04289  2/1996   (WO) .
WO 97/03096  1/1997   (WO) .
WO 97/01685  2/1997   (WO) .

OTHER PUBLICATIONS

Watasuki et al "Some organometallic chemistry of ruthenium(II)", Journal of Organometallic Chemistry 500(1995) pp. 349–362.

Schwab et al. "Synthesis and Applications of RuCl$_2$(=CHR')(PR$_3$)$_2$: The Influence of the Alkylidene Moiety on Metathesis Activity", J. Am. Chem. Soc., 1996 118, pp. 100–110.

Grunwald et al. "Five–Coordinate 16–Electron Carbene– and Vinylideneruthenium (II) Complexes Prepared from [RuCl$_2$(C$_8$H$_{12}$)]$_n$ or from the New Dihydridoruthenium(IV) Compound [RuH$_2$Cl$_2$(P$^i$Pr$_3$)$_2$]", Organometallics 1996, 15, pgs 1960–1962.

* cited by examiner

Primary Examiner—Porfirio Nazario-Gonzalez
(74) Attorney, Agent, or Firm—Keil & Weinkauf

(57) ABSTRACT

Ruthenium complexes of the formula I or IV $$RuX_2(=CH-CH_2R)L^1L^2 \quad (I)$$

$$RuXY(=CH=CH_2R)L^1L^2 \quad (IV)$$

where
  X, Y are anionic ligands,
  R is hydrogen or a substituted or unsubstituted $C_1$–$C_{20}$-alkyl radical or $C_6$–$C_{20}$-aryl radical and
  $L^1$ and $L^2$ are, independently of one another, uncharged electron donor ligands, are prepared by
    (a) reaction of RuX$_3$ with $L^1$ and $L^2$ in an inert solvent in the presence of a reducing agent and hydrogen and
    (b) reaction with compounds of the formula II $$R-C\equiv CH \quad (II)$$

where R is as defined above, in the presence or absence of water, and, if desired after isolation of the intermediate, with HY, [HL$^1$]Y or [HL$^2$]Y.

15 Claims, No Drawings

METHOD FOR PRODUCING RUTHENIUM COMPLEXES

The present invention relates to processes for preparing ruthenium complexes which can be used, for example, as catalysts in metathesis reactions.

In its simplest form, olefin metathesis (disproportionation) is a reversible, metal-catalyzed transalkylidenation of olefins by rupture and re-formation of carbon-carbon double bonds. In the metathesis of acyclic olefins, a distinction is made, for example, between self-metathesis, in which an olefine is converted into a mixture of two olefins of different molar masses (for example conversion of propene into ethene and 2-butene), and cross- or co-metathesis, which describes the reaction of two different olefins (for example of propene with 1-butene to give ethene and 2-pentene). Further application areas of olefin metathesis are syntheses of unsaturated polymers by ring-opening metathesis polymerization (ROMP) of cyclic olefins and the acyclic diene metathesis polymerization (ADMET) of α, ω-dienes. More recent applications are the selective ring opening of cyclic olefins using acyclic olefins, and also ring closure reactions (RCM) by means of which unsaturated rings of different ring sizes can be produced, preferably from α, ω-dienes.

Suitable catalysts for metathesis reactions are in principle homogeneous and heterogeneous transition metal compounds, in particular ruthenium compounds.

Heterogeneous catalysts, for example molybdenum oxide, tungsten oxide or rhenium oxide on inorganic oxidic supports, have a high activity and regenerability in reactions of non-functionalized olefins but often have to be pretreated with an alkylating agent to increase the activity when functionalized olefins such as methyl oleate are used. Olefins having protic functional groups (such as hydroxyl groups, carboxyl groups or amino groups) lead to spontaneous deactivation of the heterogeneous catalyst.

In recent years, increasing efforts have been made to prepare homogeneous catalysts which are stable in a protic medium and in the presence of atmospheric oxygen. Catalysts which have been found to be of particular interest are specific ruthenium-alkylidene compounds. Such complexes and processes of preparing them are known.

WO 93/20111 describes ruthenium- and osmium-carbene complexes for olefin metathesis polymerization. The complexes have the structure $RuX_2(=CH-CH=CR_2)L_2$. Ligands L used are triphenylphosphine and substituted triphenyl-phosphine. The preparation is carried out, for example, by reacting $RuCl_2(PPh_3)_3$ with suitable disubstituted cyclopropenes as carbene precursors. However, the synthesis of cyclopropene derivatives consists of a number of stages and is of little interest from an economic point of view.

Similar reactions are described in WO 96/04289. In addition, processes for olefin metathesis polymerization are indicated.

The use of such catalysts for peroxide-crosslinking of ROMP polymers is described in WO 97/03096.

WO 97/06185 likewise describes metathesis catalysts based on ruthenium-carbene complexes. Apart from the above-described process, they can also be prepared by reaction of $RuCl_2(PPh_3)_3$ with diazoalkanes. However, handling diazoalkanes poses a safety risk, particularly when the process is carried out on an industrial scale.

In addition, the organometallic starting materials of the formula $RuCl_2(PPh_3)_3$ have to be prepared from $RuCl_3 \cdot 3H_2O$ using a large excess of triphenylphosphine. Subsequently, $PPh_3$ ligands are again lost by ligand exchange in the catalyst synthesis itself. The carbene precursors used require multistage syntheses and do not have an unlimited shelf life.

Organometallics 1996, 15, 1960–1962 describes a process for preparing ruthenium complexes in which polymeric $[RuCl_2(cyclooctadiene)]_x$ in i-propanol is reacted with hydrogen in the presence of phosphine. This eliminates the necessity of phosphine exchange. An undefined mixture of products is obtained. In addition, long reaction times are required when starting from a polymeric starting material. The cyclooctadiene present in the organometallic starting material does not contribute to the reaction and is lost.

J. Chem. Soc. Commun. 1997, 1733–1734 describes the synthesis of a methylene complex $RuCl_2(=CH_2)(PCy_3)_2$ starting from dichloromethane and the ruthenium polyhydride $RuH_2(CH_2)_2(PCy_3)_2$. However, the ruthenium-polyhydride complex is difficult to obtain. Furthermore, long reaction times are required.

The known synthetic routes for preparing metathesis catalysts of the type $RuX_2(=CH-CH_2R)(PR'_3)_2$ are uneconomical for the reasons mentioned.

It is an object of the present invention to provide processes for preparing ruthenium alkylidene complexes of the type $RuX_2(=CH-CH_2R)L^1L^2$ or $RuXY(=CH-CH_2R)L^1L^2$, which processes lead, in a rapid and atom-economical reaction starting from readily available starting materials, to the desired products without ligand exchange. The processes should also be inexpensive and give high yields under mild reaction conditions.

We have found that this object is achieved by a process for preparing ruthenium complexes of the formula I $$RuX_2(=CH-CH_2R)L^1L^2 \qquad (I)$$

where

X is an anionic ligand,

R is hydrogen or a substituted or unsubstituted $C_1$–$C_{20}$-alkyl radical or $C_6$–$C_{20}$-aryl radical and $L^1$ and $L^2$ are, independently of one another, uncharged electron donor ligands, by (a) reaction of $RuX_3$ with $L^1$ and $L^2$ in an inert solvent in the presence of a reducing agent and hydrogen and, without isolation of intermediates, (b) subsequent reaction with compounds of the formula II $$R-C\equiv CH \qquad (II)$$

where R is as defined above, in the presence or absence of water.

This object is also achieved by a process for preparing ruthenium complexes of the formula IV $$RuXY(=CH-CH_2R)L^1L^2 \qquad (IV)$$

where

X, Y are identical or different anionic ligands,

R is hydrogen or a substituted or unsubstituted $C_1$–$C_{20}$-alkyl radical or $C_6$–$C_{20}$-aryl radical and $L^1$ and $L^2$ are, independently of one another, uncharged electron donor ligands, by (a) reaction of $RuX_3$ with $L^1$ and $L^2$ in an inert solvent in the presence of a reducing agent and hydrogen with compounds of the formula II $$R-C\equiv CH \qquad (II)$$

where R is as defined above, in the presence or absence of water, to form a compound of the formula V $$RuXH(=C=CHR)L^1L^2 \qquad (V)$$

where X, R, $L^1$, $L^2$ are as defined above, (b) separation of the compound of the formula V from the reaction mixture and subsequent reaction with HY, (HL¹)Y or (HL²)Y in an inert solvent with compounds of the formula II $$R-C\equiv CH \qquad (II)$$

where R is as defined above, in the presence or absence of water, and (c) subsequent reaction with HY, [HL¹]Y or [HL²]Y.

It has been found that the above mentioned ruthenium complexes can be obtained in very good yields directly from $RuX_3$, preferably $RuCl_3.3(H_2O)$, by simple reaction with ligands $L^1$ and $L^2$, hydrogen and terminal alkynes of the formula II in the presence of reducing agents without isolation of intermediates. The ruthenium complexes have no vinylic substituents on the carbene carbon atom. The starting materials can be prepared inexpensively and are readily available.

To prepare the mixed-anion complexes of the formula IV, the intermediate of the formula V is isolated and subsequently reacted further. This enables different ligands X and Y to be introduced.

Firstly, the reaction of $RuX_3$ with the ligands $L^1$ and $L^2$ is carried out in an inert solvent in the presence of a reducing agent and hydrogen. Solvents which can be used are aromatics, heteroaromatics, cyclic or acyclic ethers. Preferred solvents are toluene, NMP, tetrahydrofuran, dialkyl ethers, glycol ethers and dioxane. Particular preference is given to tetrahydrofuran.

The reducing agent used can be any reducing agent which reduces Ru(III) to Ru(II) under the reaction conditions. The reduction is preferably carried out using hydrogen in the presence of a metallic or nonmetallic reducing agent, preferably in the presence of an alkali metal, alkaline earth metal or transition metal, e.g. palladium or zinc, which is present in metallic form and/or can be applied to a support. The alkaline earth metals, preferably magnesium, are preferably used in an activated form. This activation can be achieved, for example, by contacting with a chlorine-containing organic solvent. For example, in a single-vessel reaction under an inert gas atmosphere, magnesium can be placed in a diluted chlorine-containing organic solvent, for example dichloroethane, and, after an induction period of from one second to 10 hours, preferably from one minute to one hour, reacted with the solvent, $RuX_3$ and the ligands $L^1$ and $L^2$ under a hydrogen atmosphere. The temperature in this reaction step (a) is preferably from 0 to 100° C., particularly preferably from 20 to 80° C., in particular from 40 to 60° C. The pressure is preferably from 0.1 to 100 bar, particularly preferably from 0.5 to 5 bar, in particular from 0.8 to 1.5 bar. The reaction is carried out for a time of preferably from 10 minutes to 100 hours, particularly preferably from 1 hour to 10 hours. The molar ratio of both ligands $L^1$ and $L^2$ as a sum to the ruthenium salt used is preferably 2–20:1, particularly preferably 2–5:1. After the reaction in step (a), the reaction mixture is reacted with a 1-alkyne, preferably at from −80 to 100° C., particularly preferably from −40 to 50° C., in particular from −30 to 20° C. In this reaction, the molar ratio of ruthenium salt originally used to 1-alkyne is preferably from 1:1 to 1:10. The reaction is preferably carried out at a pressure of from 0.1 to 10 bar, particularly preferably from 0.8 to 1.5 bar, in particular from 1 to 1.4 bar, for a time of preferably from 30 seconds to 10 hours, particularly preferably from 1 minute to 1 hour.

To prepare the complexes of the formula I, isolation of the intermediate V is not necessary, but is possible. The further reaction in step (b) is preferably carried out in the presence of water.

To prepare the mixed-anion complexes of the formula IV, the intermediate is isolated before the reaction in step (c), i.e. the reaction with HY, [HL¹]Y or [HL²]Y, preferably HY.

The reaction is usually complete after from 1 to 100 hours, preferably from 3 to 10 hours, and gives metathesis catalysts in yields of up to 95%, based on the ruthenium salt used. Suitable reactors are glass or steel vessels in general, which may have to be pressure-resistant.

The reaction mixture obtained is preferably worked up by removing volatile constituents under reduced pressure and extracting the solid residue with an organic solvent such as pentane.

In the ruthenium complexes of the formulae I and IV, X is a monodentate anionic ligand, for example halogen, pseudohalogen, carboxylate, diketonate. X is particularly preferably halogen, in particular bromine or chlorine, especially chlorine. Particular preference is given to using $RuCl_3.3H_2O$ in the reaction.

In the ruthenium complexes of the formula IV, Y can be the same ligand as X. It is preferably a halogen different from X or is a carboxyl group which is bound to a polymer or a support, thus making it possible to fix the catalyst to a support. In the case of the intermediates of the formula V, the ligand X can also be replaced by means of salt metathesis with MY, where M is an alkali metal or ammonium, preferably potassium. This also makes it possible to obtain product mixtures.

$L^1$ and $L^2$ are neutral electron donor ligands. Examples of such ligands are amines, phosphines, arsines and stibines, preferably phosphines. $L^1$ and $L^2$ are preferably selected from among phosphines of the formula III $$PR^1R^2R^3 \qquad (III)$$

where $R^1$ and $R^2$ are independently phenyl radicals or organic, sterically hindered radicals and $R^3$ is hydrogen, a substituted or unsubstituted $C_1$–$C_{20}$-alkyl radical or $C_6$–$C_{20}$-aryl radical or is as defined for $R^1$. For the purposes of the present invention, a "sterically hindered radical" is a radical which has a bulky structure. Examples of such radicals are i-propyl, tert-butyl, cyclopentyl, cyclohexyl, phenyl or menthyl. Preference is given to using a cyclohexyl radical as sterically hindered radical. Particularly preferably, all three radicals $R^1$, $R^2$ and $R^3$ are sterically hindered radicals or phenyl radicals, in particular cyclohexyl radicals. The radicals $R^1$, R and $R^3$ can each bear suitable substituents. Examples of such substituents are $C_1$–$C_6$-alkyl radicals, preferably $C_1$–$C_3$-alkyl radicals, $C_1$–$C_3$-fluoroalkyl radicals, halogen atoms, nitro groups, amino groups, ester functions and acid functions, —OH, $C_1$–$C_6$-alkoxy groups or sulfonate groups. The radicals are preferably not substituted.

The radical R is hydrogen or a substituted or unsubstituted $C_1$–$C_{20}$-, preferably $C_1$–$C_6$-alkyl radical or $C_6$–$C_{20}$-, preferably $C_6$–$C_8$-aryl radical. As regards the substituents, what has been said above applies. Particularly preferred ruthenium complexes of the formula I are $RuCl_2(=CH-CH_3)(PCy_3)_2$ and $RuCl_2(=CH-CH_2-Ph)(PCy_3)_2$ where Cy is a cyclohexyl radical and Ph is a phenyl radical.

The ruthenium complexes prepared according to the present invention can be used as metathesis catalysts.

The invention is illustrated by the examples below.

EXAMPLE 1

Synthesis of the ethylidene complex $RuCL_2(=CH-CH_3)(PCy_3)_2$ from $RuCl_3.3H_2O$ and acetylene 50 mmol of activated magnesium were placed in 20 ml of abs. THF. After addition of 8 mmol of $RuCl_3.3H_2O$, 31 mmol of tricyclohexylphosphine and 80 ml of THF, the reaction mixture was stirred at 60° C. under 1 bar of hydrogen for 6.5 hours. After cooling the reaction mixture to −30° C., acetylene was passed in for about 10 seconds and the mixture was stirred for another 5 minutes. The reaction mixture was subsequently admixed with 0.5 ml of water, warmed to room temperature, the solvent was removed under reduced pressure, the solid residue was transferred to an extraction thimble and extracted with 20 ml of pentane in a Soxhlett extractor. The yield of analytically pure, red-violet solid isolated was 5.3 g (88% of theory).

EXAMPLE 2

Synthesis of the complex $RuCl_2(=CH-CH_2-Ph)(PCy_3)_2$ from $RuCl_3 \cdot 3H_2O$ and phenylacetylene After addition of 1.9 mmol of $RuCl_3 \cdot 3H_2O$, 8 mmol of tricyclohexylphosphine and 0.5 ml of $ClCH_2CH_2Cl$ to 50 mmol of activated magnesium in 25 ml of abs. THF, the reaction mixture was stirred at 60° C. under 1 bar of hydrogen for 6.5 hours. After the reduction, the reaction mixture was cooled to −40° C. and 1.9 mmol of phenylacetylene were added dropwise, with vigorous gas evolution occurring. After stirring for 20 minutes at −40° C., the cooling was removed and, at about 0° C., 7 mmol of water were added. After warming to room temperature, stirring was continued for another 10 minutes, the solvent was subsequently removed under reduced pressure and the residue was extracted with 60 ml of toluene. The extract was evaporated to dryness, the crimson solid which remained was washed four times in succession with 10 ml each time of pentane and then twice with 40 ml each time of methanol and was dried under reduced pressure. The yield of analytically pure, crimson solid isolated was 1.2 g (76% of theory).

We claim:

1. A process for preparing ruthenium complexes of the formula I

where

X is an anionic ligand,

R is hydrogen or a substituted or unsubstituted $C_1$–$C_{20}$-alkyl radical or $C_6$–$C_{20}$-aryl radical and $L^1$ and $L^2$ are, independently of one another, uncharged electron donor ligands, by (a) reaction of $RuX_3$ with $L^1$ and $L^2$ in an inert solvent in the presence of a reducing agent and hydrogen and, without isolation of intermediates, (b) subsequent reaction with compounds of the formula II

where R is as defined above, in the presence or absence of water.

2. A process for preparing ruthenium complexes of the formula IV

where

X, Y are identical or different anionic ligands,

R is hydrogen or a substituted or unsubstituted $C_1$–$C_{20}$-alkyl radical or $C_6C_{20}$-aryl radical and $L^1$ and $L^2$ are, independently of one another, uncharged electron donor ligands, by (a) reaction of $RuX_3$ with $L^1$ and $L^2$ in an inert solvent in the presence of a reducing agent and hydrogen with compounds of the formula II

where R is as defined above, in the presence or absence of water, to form a compound of the formula V

where X, R, $L^1$, $L^2$ are as defined above, (b) separation of the compound of the formula V from the reaction mixture and subsequent reaction with HY, $(HL^1)Y$ or $(HL^2)Y$ in an inert solvent with compounds of the formula II

where R is as defined above, in the presence or absence of water, and (c) subsequent reaction with HY, $[HL^1]Y$ or $[HL^2]Y$.

3. A process as claimed in claim 1, wherein $L^1$ and $L^2$ are selected from among phosphines of the formula III

where $R^1$ and $R^2$ are, independently of one another, phenyl radicals or organic, sterically hindered radicals and $R^3$ is hydrogen, a substituted or unsubstituted $C_1$–$C_{12}$-alkyl radical or $C_6$–$C_{20}$-aryl radical or is as defined for $R^1$.

4. A process as claimed in claim 3, wherein $R^1$ and $R^2$ are selected from among i-propyl, tert-butyl, cyclopentyl, cyclohexyl, phenyl or menthyl.

5. A process as claimed in claim 1, wherein X is halogen and Y is the same or different halogen or is a carboxyl group which is bound to a polymer or a support.

6. A process as claimed in claim 1, wherein the reduction with hydrogen is carried out in the presence of a metallic or nonmetallic reducing agent.

7. A process as claimed in claim 6, wherein the reducing agent used is magnesium which is activated by contacting with a chlorine-containing organic solvent.

8. A process as claimed in claim 1, wherein the reaction in step (a) is carried out at a pressure in the range from 0.1 to 100 bar and that in step (b) is carried out at a pressure in the range from 0.1 to 10 bar.

9. A process as claimed in claim 1, wherein the reaction in step (a) is carried out at from 0 to 100° C. and that in step (b) is carried out at from −80 to 100° C.

10. A process as claimed in claim 1, wherein the solvent is selected from aromatics, heteroaromatics, cyclic or acyclic ethers.

11. A process as claimed in claim 1, wherein the ruthenium complexes of the formula I or IV are, after removal of volatile constituents from the reaction mixture, isolated in analytically pure form by extraction with an organic solvent.

12. A process as claimed in claim 2, wherein $L^1$ and $L^2$ are selected from among phosphines of the formula III

where $R^1$ and $R^2$ are, independently of one another, phenyl radicals or organic, sterically hindered radicals and $R^3$ is hydrogen, a substituted or unsubstituted $C_1$–$C_{12}$-alkyl radical or $C_6$–$C_{20}$-aryl radical or is as defmed for $R^1$.

13. A process as claimed in claim 12, wherein $R^1$ and $R^2$ are selected from among i-propyl, tert-butyl, cyclopentyl, cyclohexyl, phenyl or menthyl.

14. A process as claimed in claim 2, wherein X is halogen and Y is the same or different halogen or is a carboxyl group which is bound to a polymer or a support.

15. A process as claimed in claim 2, wherein the reduction with hydrogen is carried out in the presence of a metallic or nonmetallic reducing agent.

* * * * *